United States Patent
Peeler et al.

(10) Patent No.: US 6,871,516 B2
(45) Date of Patent: Mar. 29, 2005

(54) ANTI-SLIP GARMENT

(75) Inventors: Donald Hoover Peeler, Charlotte, NC (US); Stefan Bodenschatz, Buxtehude, DE (US); Bruce Alan Reed, Hickory, NC (US)

(73) Assignee: BSN-JOBST, Charlotte, NC (US)

( * ) Notice: Subject to any disclaimer, the term of this patent is extended or adjusted under 35 U.S.C. 154(b) by 315 days.

(21) Appl. No.: 10/145,497

(22) Filed: May 14, 2002

(65) Prior Publication Data

US 2003/0213269 A1 Nov. 20, 2003

(51) Int. Cl.$^7$ ................................................. D04B 1/00
(52) U.S. Cl. ............................. 66/171; 66/172; 66/177; 66/173; 66/178
(58) Field of Search ............................... 66/172 E, 177, 66/173, 178 R, 178 A, 182; 442/101, 304, 305, 306; 602/76, 75, 63, 62

(56) References Cited

U.S. PATENT DOCUMENTS

| | | | |
|---|---|---|---|
| 3,392,553 A | | 7/1968 | Burleson |
| 3,611,755 A | * | 10/1971 | Millar ........................ 66/173 |
| 3,728,875 A | | 4/1973 | Hartigan et al. |
| 3,729,956 A | * | 5/1973 | Nebel et al. .............. 66/172 E |
| 3,874,001 A | | 4/1975 | Patience et al. |
| 3,975,929 A | | 8/1976 | Fregeolle |
| 3,983,870 A | | 10/1976 | Herbert et al. |
| 4,021,860 A | | 5/1977 | Swallow et al. |
| 4,048,818 A | | 9/1977 | Cueman |
| 4,086,790 A | | 5/1978 | Hanrahan, Jr. et al. |
| 4,149,274 A | | 4/1979 | Garrou et al. |
| 4,180,065 A | | 12/1979 | Bowen |
| 4,180,869 A | | 1/1980 | Pedergrass et al. |
| 4,502,158 A | | 3/1985 | Mouri et al. |
| 4,561,267 A | | 12/1985 | Wilkinson et al. |
| 5,022,387 A | | 6/1991 | Hasty |
| 5,412,957 A | | 5/1995 | Bradberry et al. |
| 5,540,063 A | * | 7/1996 | Ferrell ....................... 66/172 E |
| 5,814,003 A | | 9/1998 | Knox et al. |
| 5,885,910 A | | 3/1999 | Graichen |
| 5,948,707 A | | 9/1999 | Crawley et al. |
| 6,178,785 B1 | | 1/2001 | Samata |

FOREIGN PATENT DOCUMENTS

| | | |
|---|---|---|
| DE | 199 40 018 A1 | 3/2001 |
| DE | 199 40 019 A1 | 3/2001 |
| GB | 1 532 894 A | 11/1978 |

OTHER PUBLICATIONS

International Search Report.

* cited by examiner

Primary Examiner—Danny Worrell
(74) Attorney, Agent, or Firm—Alston & Bird LLP

(57) ABSTRACT

There is provided a therapeutic medical compression garment with an integrally knit anti-slip portion. The anti-slip portion of the garment is located in the upper area thereof. In the embodiment wherein the garment is a stocking, the anti-slip portion is placed in the thigh area of the thigh-hi stocking or the upper calf area of the knee-hi stocking. In the thigh-hi stockings, the anti-slip section may start just above the knee or be located in the upper thigh area (for use in mobilized patients, the anti-slip section may start already just above) the ankle area, e.g., also in knee-hi stockings at the calves upwards.

22 Claims, 5 Drawing Sheets

ANTI-SLIP GARMENT

FIELD OF THE INVENTION

The present invention relates to an anti-slip therapeutic medical compression garment. More particularly, the present invention relates to a therapeutic gradient compression stocking having a high friction yarn knit into a portion of the stocking so as to contact the skin of the wearer.

BACKGROUND OF THE INVENTION

Therapeutic medical compression garments are used on a relatively wide scale to assist in the management of venous and lymphatic disorders. The purpose of such stockings is to counter the effects of elevated pressures internally within the human anatomy caused by gravity or disease processes. They may also be applied to inactive, bedridden individuals to help prevent a thromboembolic event. The purpose of such garments in this case is to maintain directional flow of blood, thereby helping to reduce the risk of thrombus formation in the superficial and deep veins.

More specifically, therapeutic stockings typically have a rather precisely defined and controlled pressure profile to effect a predetermined compression of the interstitium of the leg. The custom Venous Pressure Gradient Stocking was developed by Conrad Jobst, a sufferer of venous disease. Mr. Jobst found relief from his problem while standing in a swimming pool. Mr. Jobst reasoned that the water pressure in the pool, which increases with depth, cancelled out the internal pressure in the veins of his leg. Jobst and others identified a need to apply relatively large compression force in proximity to the ankle.

Therapeutic medical gradient compression garments are designed to provide sufficient external circumferential counter pressure to maintain the venous and lymphatic pressures at a more normal level in the extremity, thus assisting the movement of venous blood and lymph from the extremity. Another important effect of compression is the reduction of venous volume. Reduction of venous volume leads to an increase of venous flow velocity. While the exact mechanism of action of gradient compression therapy remains unknown, improvements in skin and subcutaneous tissue microcirculatory hemodynamics may contribute to the benefits of compression therapy. The direct effect of compression on subcutaneous pressure is a plausible mechanism. Edema reduction and edema prevention is the goal in patients with chronic venous insufficiency, lymphedema, and other edema causing conditions. Subcutaneous pressures increase with elastic compression. This rise in subcutaneous tissue pressure acts to counter transcapillary Starling forces, which favor leakage of fluid out of the capillary.

There are a variety of therapeutic medical gradient compression garments on the market today. For example, stockings of various descriptions have been proposed. Unfortunately, therapeutic stockings have a tendency to slip down the leg of the wearer, thereby detracting from the benefits of the stocking. An example of a therapeutic stocking is described in U.S. Pat. No. 3,975,929 to Fregeolle which describes a thigh length anti-embolism stocking made with alternating courses of covered spandex yarn on a circular hosiery knitting machine. The stocking described in Fregeolle shows a turned welt around a portion of the top of the stocking and a narrow elastic band stitched to the upper portion of the stocking. The inner face of the elastic band is provided with beads or rows of frictional gripping material that aid in supporting the upper end of the stocking on the leg of the wearer by frictionally engaging the leg.

Another example of a therapeutic stocking is described in U.S. Pat. No. 3,874,001 to Patience, et al., which discloses a full length stocking having a foot and leg portion made from circumferential elastic. A narrow band of non-slip elastomeric webbing material is sewn to the upper end of the leg portion by over stitching. The particular stitching used is said to provide for adequate "play" in the stitching to insure the deformation of the stocking as it is worn.

In U.S. Pat. No. 3,983,870 to Herbert, et al. there is disclosed a slip-resistant support for limbs, especially a medical stocking. Herbert, et al. address the slip problem by coating 20 to 30 percent of the leg portion of the outer parts of the inner surface of the knitted thread. The inner surface is coated with a non-adhesive, non-continuous, relatively soft elastomeric polymeric material with a high coefficient of friction to skin so as to provide a nonocclusive slip resistant surface capable of maintaining the support in place on the limb of the body.

Another type of anti-embolism stocking is disclosed in U.S. Pat. No. 3,728,875 to Hartigan, et al. This stocking is knit on a circular hosiery knitting machine and the upper portion is slit downwardly in a walewise direction and a wedge shaped insert of soft elastic fabric is sewn into the slit to increase the circumference of the upper end of the stocking. In stockings of this type the sewing of the wedge increases the cost of production. The insert is formed of a different compressive fabric than the remaining portion of the upper end of the stocking so that the portion of the leg covered by the insert does not receive the same compressive force as applied to the remaining portion of the leg of the wearer. The stocking also has a partial round of elastic retention band made with a corrugated anti-slip inner surface of urethane elastomer sewn to the upper narrow welt of the stocking proper, projecting above the stocking welt so that its top forms a continuous line with the top of the insert.

Although strides have been made in improving the anti-slipping properties of anti-embolism garments, application of elastomeric bands requires a separate manual sewing operation, which increases the costs of production. Thus, there remains a need for an effective, inexpensive therapeutic medical compression garment that will resist slipping down the leg of the wearer.

SUMMARY OF THE INVENTION

With the foregoing in mind, it is an object of the present invention to provide a therapeutic garment having effective anti-slip properties. It is also an object of the invention to provide a therapeutic medical compression stocking which does not require sewing a separate elastomeric portion to the upper end of the stocking. Another object of the present invention is to provide an anti-slip garment devoid of structures that could cause high pressure points, such as with bulky seams, band overlaps/joints, or strips or dots of silicone. Still another object of the present invention is to provide an anti-slip garment that is seamless and, therefore, eliminates the seam necessary to attach a sewn on band. A still further object of the present invention is to provide an anti-slip garment that is free from elastic bands and from silicone friction strips or dots which are potential source of constriction and skin irritation and even potential skin damage.

In accordance with the present invention there is provided a therapeutic medical gradient compression garment with an integrally knit anti-slip portion. The anti-slip portion is formed as part of the garment's body fabric. Therapeutic medical gradient compression garments include any garments, such as stockings, sleeves, and the like, for use on a patient to assist in the prevention management of venous or lymphatic disorders and/or thrombosis in the limb of a patient. The knit anti-slip portion of the garment typically includes one jersey course of so-called "locking yarn," a tuck and float "high friction" yarn or combinations of such yarns, and one (or more) jersey course(s) of so called "body yarn(s)". In this way the high friction yarn(s) are exposed to the inner surface of the garment to contact the limb of the wearer.

The body of the garment is knit in any of the usual ways known to those skilled in the art, such as jersey stitches. However, it should be understood that other knitting patterns may be used. One such way of forming the body of the garment is to knit the upper portion of the garment with alternate courses of bare or covered elastomeric yarn and intervening courses of stretchable textured yarn. The elastomeric yarn is tucked in the even wales and is knit in the odd wales of every other course. The stretchable textured yarn is knit in jersey courses.

In a preferred embodiment, that of a stocking, the anti-slip portion is located in the upper area of the stocking, i.e., in the thigh area of the thigh-hi stocking or the upper calf area of the knee-hi stocking. In thigh-hi stockings, the anti-slip portion may start just above the knee, similarly, in knee-hi stockings the anti-slip portion may start just above the ankle area. In both styles of stockings the anti-slip portion is knit on the interior of the stocking. In another embodiment, the stocking has a turned welt that includes the anti-slip portion. In this embodiment the anti-slip portion is knit on the exterior face of the welt and then turned inward, against the wearer's skin. Furthermore, it is helpful to construct the welt to make it less likely to roll back on itself and down the leg. In this embodiment the elastomeric lay-in yarn in a few of the courses preceding and following the welt fold, is fed in at a reduced rate, for example, a 10% reduction in elastomer feeder speed, than in the courses that form the remainder of the welt. This causes the fold or top of the welt to neck in.

The body yarn may be cotton, textured nylon or such other yarns known to those skilled in the art. The high friction (anti-slip) yarn(s) can be made of all types of elastomeric material having high frictional coefficient, e.g., spandex, SEBS, rubber, neoprene or isoprene. Combining more than one of the high friction yarns together increases the cross-sectional dimension and thus the surface area contacting the skin. The locking yarn is knit as a jersey course before and/or after the tuck and float bare elastomeric yarn and is used to hold the high friction yarn in place. The locking yarn is a yarn with sufficient elastic properties, preferably a covered elastomeric yarn.

The loops of the locking yarn secure the high friction yarn(s) in the knit structure. With this knit construction, it is more difficult to pull the tuck and float elastomeric yarn(s) out of the knit structure. This increases the durability of the anti-slip section significantly and also results in an enhanced fastness against slippage of the high friction yarn(s) during washing.

BRIEF DESCRIPTION OF THE DRAWINGS

Other features and advantages of the present invention will become apparent in the following detailed description of the embodiments of the invention when taken in conjunction with the accompanying drawings.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Figure 1:
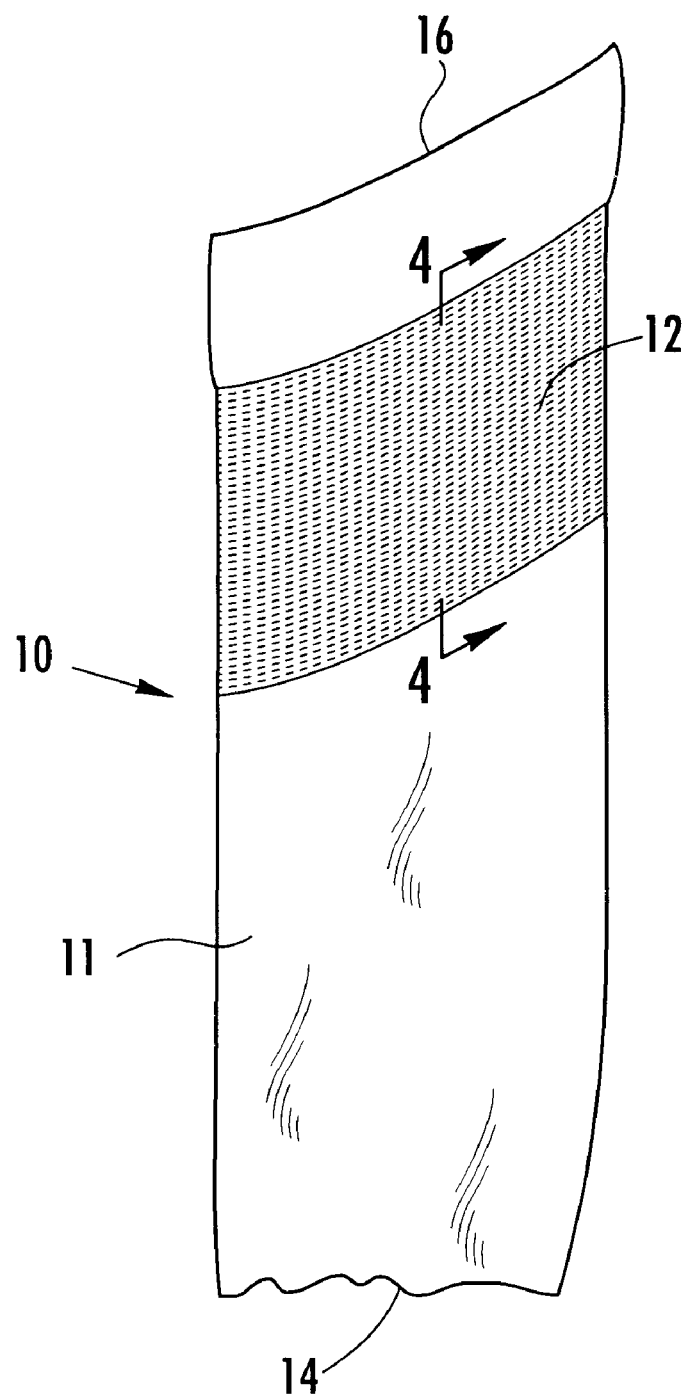
FIG. 1 is an isometric view of a medical compression garment of this invention illustrating an anti-slip portion on the interior of the garment.

In accordance with the present invention there is provided a therapeutic medical gradient compression garment with an integrally knit anti-slip portion. With reference to the attached drawings there is shown in FIG. 1 a therapeutic medical garment 10 of the present invention. Therapeutic medical compression garments include any garments, such as stockings, sleeves, and the like, for use on a patient to assist in the management of venous or lymphatic disorders and/or thrombosus in the limb of a patient. As shown, the garment 10 has a body portion 11 and an anti-slip portion 12 formed as part of the garment's body fabric located toward the upper end 16 thereof. The garment 10 may be a gradient compression sleeve that fits over the arm of the wearer.

The body 11 of the garment 10 is knit in any of the usual ways known to those skilled in the art, such as jersey stitches. However, it should be understood that other knitting patterns may be used. One such way of forming the body of the garment is to knit the upper portion of the garment with alternate courses of bare or covered elastomeric yarn and intervening courses of stretchable textured yarn. The elastomeric yarn is tucked in the even wales and is knit in the odd wales of every other course. The stretchable textured yarn is knit in jersey courses. The therapeutic stocking of this invention may be knit on any conventional knitting machine, such as a Santoni Pendolina Medical. The anti-slip portion in contact with the user's skin may be knit using a 2×1 tuck float stitch. Alternatively, a 3×1 or 4×1 tuck float stitch may be used.

Figure 4:
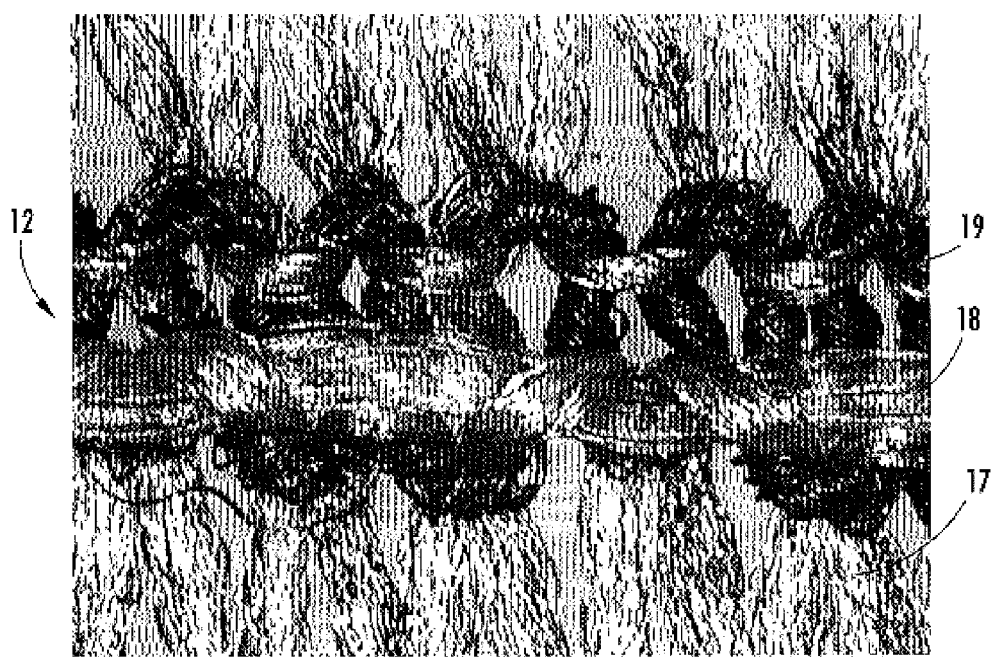
FIG. 4 is a photomicrogram of a generally enlarged view of a fragmentary portion of the fabric showing the anti-slip portion taken along lines 4—4 of FIG. 1 made of a knit structure with a covered locking yarn and a spandex elastomeric yarn in a 2×1 tuck float selection.

Turning now to FIG. 4, there is shown an enlargement of a portion of the anti-slip portion 12 of the invention. The knit anti-slip portion 12 of the garment 10 typically includes one jersey course of so-called "locking yarn" 19 (black yarn), a tuck and float "high friction" yarn 18, and one (or more) jersey course(s) of so called "body yarn(s) 17. In this way the high friction yarn is exposed to the inner surface of the garment to contact the limb of the wearer. The therapeutic garment may be knit so that it is graduated in size from the lower end 14 to the upper end 16. Alternatively, the therapeutic garment 10 may be knit so that the garment is graduated in pressure from one end to the other. Of course, the garment 10 may be knit so as to be graduated in both size and pressure.

The body yarn 17 may be cotton, textured nylon or such other yarn known to those skilled in the art. The high friction yarn 18 can be made of all types of elastomeric yarn having high frictional coefficient, e.g., spandex, SEBS, rubber, neoprene or isoprene. Examples of the elastomeric yarn used in the inlay courses are Clearspan® spandex manufactured by Radici, Lycra® spandex manufactured by DuPont, Dorlastain® spandex manufactured by Bayer, or any other applicable spandex yarn. Japanese Patent No. 04 018 119 describes a special anti-slip yarn made of alkalene, terephthalate hard segment and an aliphatic polyether and/or aliphatic polyester soft segment.

The locking yarn 19 is knitted as a jersey course before or after the tuck and float bare elastomeric yarn. The locking yarn is a yarn with sufficient elastic properties, preferably a covered (with synthetic or natural yarn) elastomeric yarn. Other locking yarns that may be used in this invention are fusible yarns, for instance, low melt nylon, polypropylene or other yarns that can be melted at the reasonable processing temperatures. The fusible yarn can be by itself or in combination with other synthetic or natural yarns, including elastomeric. The loops of the locking yarn secure the yarn in the knit structure. With this knit construction, it is more difficult to pull the tuck and float bare elastomeric yarn out of the knit structure. This increases the durability of the anti-slip section significantly and also results in a high fastness against washing. The preferred locking yarn 19 is an elastomeric covered yarn because such covered yarns have a larger cross-section and are more durable. The increased dimensions of the locking yarn pushes against the higher friction yarn, enhancing contact with the wearer's skin.

Figure 2:
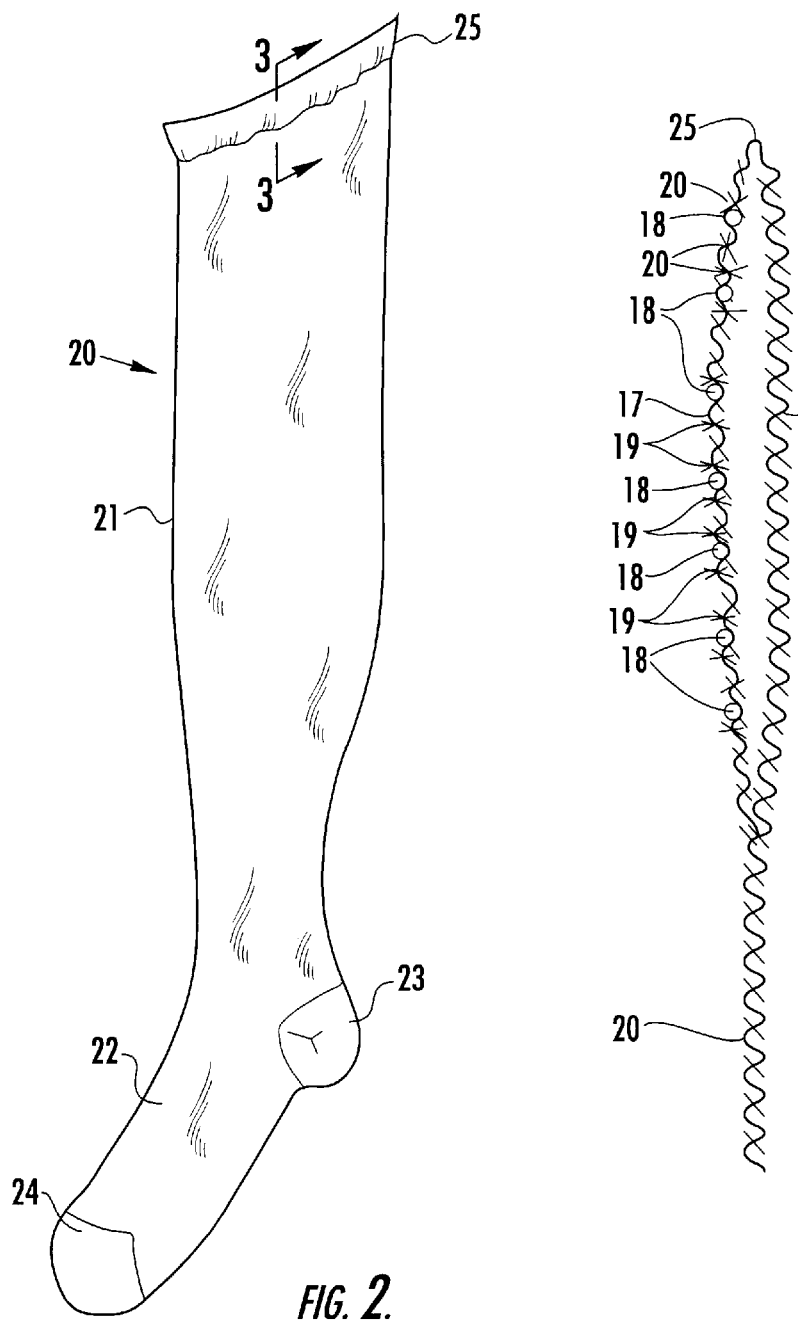
FIG. 2 is an isometric view of an embodiment of this invention showing a therapeutic stocking illustrating the manner in which the integrally knit turned welt extends above the level of the upper end of the leg of the stocking providing contact of the high friction yarn with the skin.

In one of the preferred embodiments of the present invention, that embodiment described in FIG. 2, the therapeutic medical compression garment is a stocking 20. As shown in FIG. 2, the stocking 20 includes a leg portion 21 and a foot portion 22. The foot portion 22 includes a heel pocket 23 and a toe pocket 24. The upper end of the leg portion 21 of the medical stocking has an anti-slip portion 25 and an integrally knit turned welt for knee length or thigh length stockings which also contains an anti-slip portion (FIG. 3, when the welt is turned the bare elastomeric yarn contacts the wearer's skin when the stocking is worn thereby increasing the anti-slip properties of the stocking). The foot portion 22 and the leg portion 23 of the stocking 20 may be knit of any suitable stitch construction that provides a graduated compressive force on the leg of the wearer.

Figure 3:
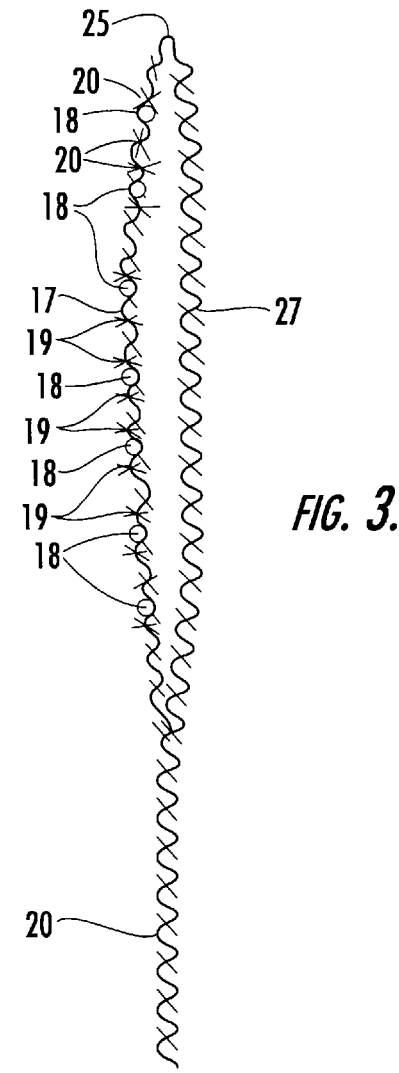
FIG. 3 is an enlarged vertical section taken substantially along lines 3—3 in FIG. 2 and illustrating the inner and outer plies of the turned welt extension and showing the elastomeric yarns.

As shown in FIG. 3 there is upper leg portion 21 and extending therefrom is an outer welt portion 27 formed generally in a conventional manner with a covered spandex yarn (body yarn 17). In the turned portion of the welt 25 a high friction yarn 18 is "pushed" to the outside and held in place by a locking yarn 19. The high friction yarn is exposed to the inner surface of the welt to contact the skin. In addition, it is helpful to construct the welt to make it less likely to roll back on itself and down the leg. In this embodiment the knit courses going into and out of the welt fold are made tighter than the preceding and following courses that form the remainder of the welt. This causes the fold or top of the welt to neck in.

One desirable construction of the leg and foot portions of the stocking is to knit a stretchable textured yarn in a jersey pattern, a bare elastomeric yarn laid-in in an alternating one by one pattern, and knit a stretchable textured yarn in a jersey pattern on one or more feeds thereafter. It is to be understood that any combinations of stitch constructions may be knit in the leg and foot portions of the stocking.

Figure 5:
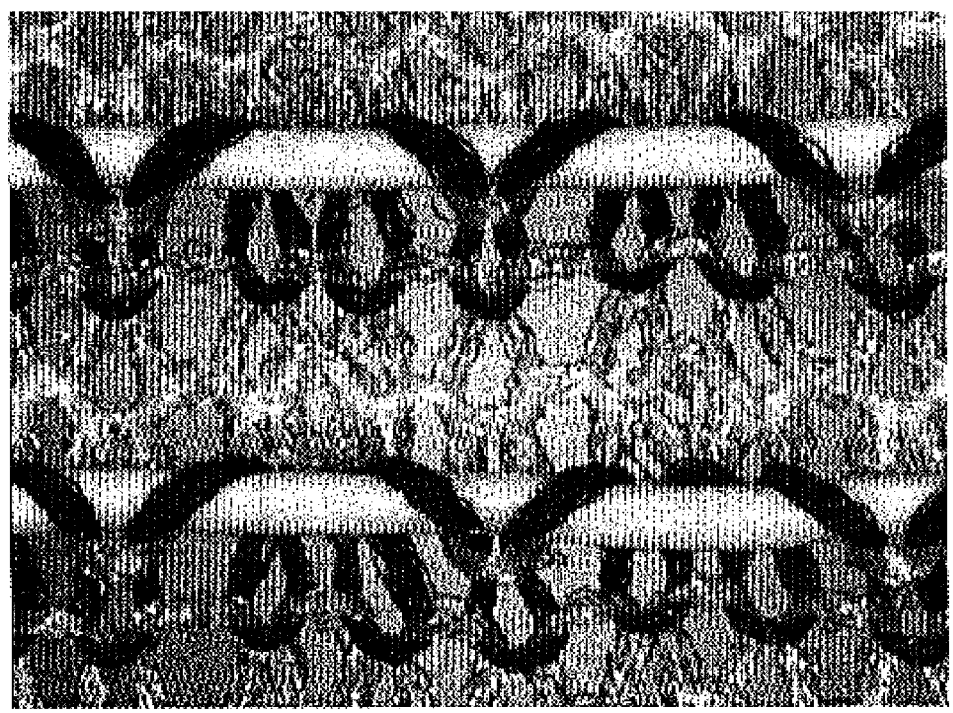
FIG. 5 is a photomicrogram of a generally enlarged view of a fragmentary portion of the fabric showing an anti-sip portion made of a knit structure with a textured nylon locking yarn and rubber elastomeric yarn in a 2×1 tuck-float selection.

In another embodiment, that shown in FIG. 5, there is a photomicrogram showing a fragmentary portion of a knit structure having a high friction rubber elastomeric yarn and textured nylon locking yarn having a 2×1 tuck-float.

Figure 6:
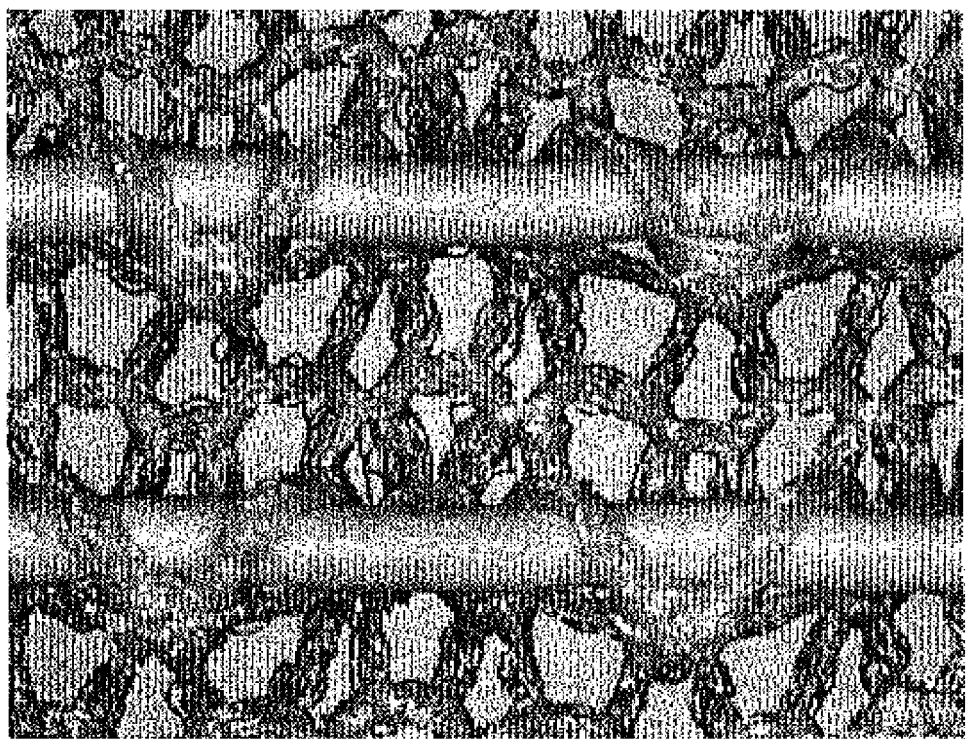
FIG. 6 is a photomicrogram of a generally enlarged view of a fragmentary portion of a knit structure showing an anti-slip portion made with a covered spandex locking yarn and neoprene elastomeric yarn in a 2×1 tuck-float selection.

In FIG. 6 there is shown yet another embodiment of the present invention wherein there is a portion of a knitted garment having an anti-slip area knitted therein where the high friction yarn is a neoprene elastomeric yarn and the locking yarn is a covered spandex having a 2×1 tuck-float.

EXAMPLE 1

A therapeutic stocking of the present invention was knit with a jersey knit structure on a conventional circular knit hosiery machine. The leg yarn was nylon. The inlay yarn was bare spandex. The upper portion of the stocking contained a high friction yarn made of spandex. The covered locking yarns were knit in a 2×1 tuck float selection as shown in FIG. 4.

The leg portion of the stocking exerted a compressive pressure of from 18 mm Hg at the ankle and gradually decreased to 8 mm Hg at the upper thigh.

Slippage tests on the garments were conducted as follows: an upper portion of a garment was donned over a cylinder with the diameter corresponding to limb girth. When the garment was pulled from the cylinder by the tensile testing machine, the maximum force necessary to start the garment moving was recorded. This force is a measure of the resistance of the garment to slide. The lower the force the easier it is to slide.

| Comparison of the Properties of Sewn and Knitted Anti-Slip Bands | | | | |
| --- | --- | --- | --- | --- |
| Product | Size/Design | Pressure at welt, mm Hg | Slip force, kg | Relative slip force per mm Hg of pressure |
| Sewn on band | Medium Regular | 8.0 | 2.07 | 0.259 |
| | | 6.3 | 1.56 | 0.247 |
| Sewn on band | Medium Long | 8.0 | 1.78 | 0.222 |
| Locking yarn flat | Medium Regular | 6.0 | 1.94 | 0.323 |

| | | -continued | | |
|---|---|---|---|---|
| nylon cover | Medium Long | 6.2 | 2.09 | 0.338 |
| Locking yarn textured nylon cover | Medium Regular | 4.0 | 1.54 | 0.384 |
| Herringbone welt | Medium Regular | 5.1 | 1.53 | 0.300 |
| Ribbed welt | Medium Regular | 5.9 | 1.69 | 0.286 |

Comparison of the compression under the welt (mm Hg):

| Circumference by size chart | Min | Avg. | Max |
|---|---|---|---|
| Sewn in welt | | | |
| Size Small Reg | 2.2 | 8.2 | 9.4 |
| Medium Regular | 6.8 | 7.8 | 10.1 |
| Large Regular | 4.6 | 6.0 | 9.5 |
| Knitted Welt | | | |
| Herringbone welt | 4.6 | 7.8 | 9.0 |
| Ribbed welt | 4.7 | 8.1 | 9.2 |

Resistance to sliding is also proportional to the applied fabric tension. A relative sliding resistive force can thus be determined by normalizing the pull force to the applied pressure. As seen from the results in the tables above, the garments with anti-slip portions provided by this invention have superior anti-slip properties. The proposed design of a wide "anti-slip knit-in zone" provides gentle friction power without the increased pressure typical of elastic bands because it allows for distribution of a lighter staying force over a greater surface area. As a result, stockings are kept in place without binding. This virtually eliminates discomfort and potential injury associated with constricting bands.

Another benefit of the proposed design is that it is seamless and, therefore, eliminates the band seam necessary to attach the sewn on band. There are no pressure points at fabric overlap that potentially can lead to skin breakdown or tissue damage.

One other benefit of the proposed design is that it creates a construction free from elastic bands and from silicone friction strips or dots which are potential source of constriction and skin irritation and even potential skin damage. Absence of silicone dots that create pressure points on skin results in absence of pinching, rash or prickly heat irritation, and pulling of leg hairs. The knitted welt fabric is breathable, soft and comfortable as opposed to solid silicone strips.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A therapeutic medical garment comprising a knitted garment having a knitted anti-slip portion, said anti-slip portion comprising a body yarn, a high friction yarn and a locking yarn wherein high friction yarn is held in position with said locking yarn such that said high friction yarn contacts the wearer's skin so as to increase the anti-slip properties of the garment, said garment being graduated in pressure from one end to the other.

2. The therapeutic garment according to claim 1 wherein said garment is a sleeve.

3. The therapeutic garment according to claim 1 wherein said garment is a stocking.

4. The therapeutic garment according to claim 1 wherein said garment is graduated in size from one end to the other.

5. The therapeutic garment according to claim 1 wherein said high friction yarn is spandex and said locking yarn is a spandex yarn covered with nylon.

6. The therapeutic garment according to claim 1 wherein said high friction yarn is a rubber yarn and said locking yarn is a spandex yarn covered with nylon.

7. The therapeutic garment according to claim 1 wherein said high friction yarn is neoprene yarn and said locking yarn is a spandex yarn covered with nylon.

8. The therapeutic garment according to claim 1 wherein said high friction yarn is spandex and said locking yarn is a fusible yarn.

9. The therapeutic garment according to claim 1 wherein said side of said anti-slip portion in contact with the user's skin is knit using a 2×1 tuck float stitch.

10. The therapeutic garment according to claim 1 wherein said side of said anti-slip portion in contact with the user's skin is knit using a 3×1 tuck float stitch.

11. The therapeutic garment according to claim 1 wherein said side of said anti-slip portion in contact with the user's skin is knit using a 4×1 tuck float stitch.

12. A therapeutic medical stocking comprising a foot portion, a leg portion having an integrally knit turned welt, said leg portion being knit so that the pressure in the foot portion is graduated from the foot portion to the turned welt portion, said turned welt portion having an anti-slip portion, said anti-slip portion comprising a body yarn, a high friction yarn and a locking yarn wherein high friction yarn is held in position with said locking yarn such that said high friction yarn contacts the wearer's skin so as to increase the anti-slip properties of said stocking.

13. The therapeutic stocking according to claim 12 wherein said turned welt is constructed such that several knit courses, preceding and following the welt fold, have a 10% reduction in elastomer feeder speed.

14. The therapeutic stocking according to claim 12 wherein said anti-slip portion is a turned welt knit with a high friction yarn and a locking yarn.

15. The therapeutic stocking according to claim 12 wherein said stocking is graduated in size from one end to the other.

16. The therapeutic stocking according to claim 12 wherein said high friction yarn is spandex and said locking yarn is a spandex yarn covered with nylon.

17. The therapeutic stocking according to claim 12 wherein said high friction yarn is a rubber yarn and said locking yarn is a spandex yarn covered with nylon.

18. The therapeutic stocking according to claim 12 wherein said high friction yarn is neoprene yarn and said locking yarn is a spandex yarn covered with nylon.

19. The therapeutic stocking according to claim 12 wherein said high friction yarn is spandex and the said locking yarn is a fusible yarn.

20. The therapeutic stocking according to claim 12 wherein said side of said anti-slip portion in contact with the user's skin is knit using 2×1 tuck float stitch.

21. The therapeutic stocking according to claim 12 wherein said side of said anti-slip portion in contact with the user's skin is knit using a 3×1 tuck float stitch.

22. The therapeutic stocking according to claim 12 wherein said side of said anti-slip portion in contact with the user's skin is knit using a 4×1 tuck float stitch.

* * * * *